United States Patent [19]

Scheuer et al.

[11] Patent Number: 6,011,010

[45] Date of Patent: *Jan. 4, 2000

[54] CYTOTOXIC AND ANTIVIRAL COMPOUND

[75] Inventors: Paul J Scheuer; Mark T Hamann, both of Honolulu, Hi.; Dolores G. Gravalos, Madrid, Spain

[73] Assignee: Pharma Mar, s.a., Madrid, Spain

[*] Notice: This patent is subject to a terminal disclaimer.

[21] Appl. No.: 08/935,073

[22] Filed: Sep. 25, 1997

Related U.S. Application Data

[63] Continuation of application No. 08/192,569, Feb. 3, 1994.

[51] Int. Cl.[7] .............................. A61K 38/12; C07K 7/64
[52] U.S. Cl. .................................... 514/11; 514/9; 514/2; 530/321; 530/317; 930/DIG. 546; 930/DIG. 548
[58] Field of Search ..................................... 530/317, 321; 514/11, 9, 2; 930/DIG. 546, 548

[56] References Cited

PUBLICATIONS

Hamann et al, J. Am. Chem. Soc., 115, pp. 5825–5826, (1993).
Merck Manual, 11th ed., pp. 761–63; 1368–71; 456–459.
Merck Manual, 11th ed., pp. 761–763; 1368–1371; 456–459.

*Primary Examiner*—Keith D. MacMillan
*Assistant Examiner*—T. D. Wessendorf
*Attorney, Agent, or Firm*—Ernest V. Linek; Banner & Witcoff, Ltd.

[57] ABSTRACT

Kalahide F. of formula I below, may be isolated from a secoglossan. The compound may be used in the manufacture of pharmaceutical compositions or in the treatment of tumors or viral conditions.

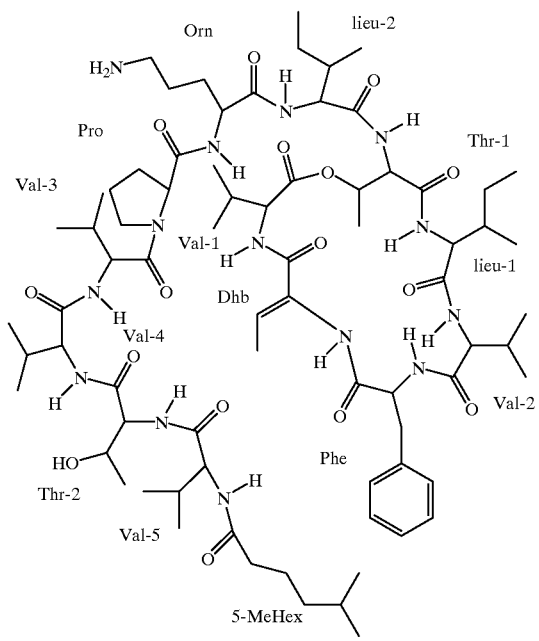

4 Claims, No Drawings

CYTOTOXIC AND ANTIVIRAL COMPOUND

This is a continuation of application Ser. No. 08/192,569 filed on Feb. 3, 1994.

This invention is concerned with a cytotoxic and antiviral compound isolated from the sacoglossan, *Elysia rafescens*.

According to the invention there is provided, a new compound, the peptide, Kalahide F, of the formula:

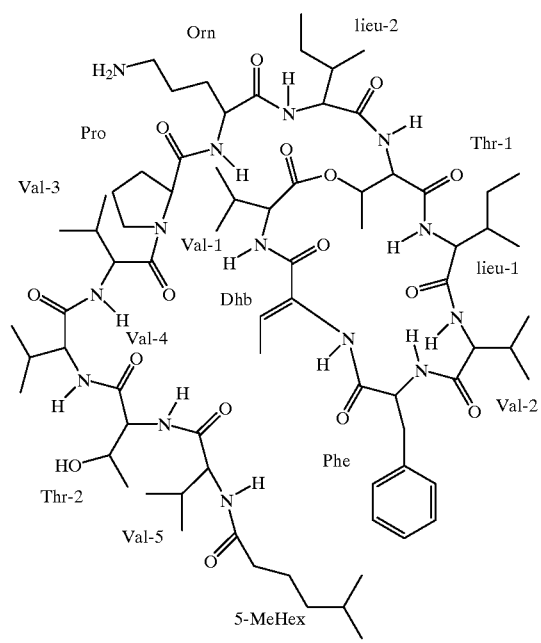

The antitumor activities of this compound have been determined "in vitro" in cell cultures of human lung carcinoma A-549 and human colon carcinoma HT-29. The procedure was carried out using the methodology described by Raymond J. Bergeron et al., *Biochem. Biophys. Res. Comm.* 1984, 121 (3), 848–854 and by Alan C. Schroeder et al., *J. Med. Chem.* 1981, 224 1078–1083.

The antiviral activities of this compound have also been determined "in vitro" against HSV (Herpes simplex virus) and VSV (Vesicular stomatitis virus). The methodology used to carry out this determination is described by Raymond J. Bergeron et al., *Biochem. Biophys. Res. Comm.* 1984, 121 (3), 848–854 and by Alan C. Schroeder et al. *J. Med. Chem.* 1981, 224 1078–1083.

Therefore, the present invention also provides a method of treating any mammal affected by a malignant tumor sensitive to compound above described, which comprises administering to the affected individual a therapeutically effective amount of these compounds or a pharmaceutical composition thereof, and a method of treating viral infections in mammals, comprising administering to a patient in need of such treatment, an antiviral effective amount of the compounds described in the present invention.

The present invention also relates to pharmaceutical preparations which contain as active ingredient these compounds, or a pharmaceutically acceptable acid addition salt thereof, as well as the process for its preparation.

Examples of pharmaceutical compositions include any solid (tablets, pills, capsules, granules, etc.) or liquid (solutions, suspensions or emulsions) suitable composition for oral, topical or parenteral administration, and they may contain the pure compound or in combination with any carrier or other pharmacologically active compounds. These compositions may need to be sterile when administered parenterally.

The correct dosage of a pharmaceutical composition of these compounds will vary according to the particular formulation, the mode of application and particular situs, host and tumor being treated. Other factors like age, body weight, sex, diet, time of administration, rate of excretion, condition of the host, drug combinations, reaction sensitivities and severity of disease shall be taken in account. Administration can be carried out continuously or periodically within the maximum tolerated dose. Kahalalide F was isolated from the sacoglossan, *Elysia rufescens* (family Plakobranchidae, order Sacoglossa), collected near Black point, Oahu. This animal varies in size between 1 and 4 cm; it is dark red-brown in color with light-colored spots. There is orange fringing of the parapodia, which have very small dark green spots from sequestered chloroplasts. *Elysia rufescens* feeds on the delicate, feather-like green alga Bryopsis sp. Kahalalide F can also be isolated from this alga. Two hundred animals were collected over the period of several weeks during spring, 1991 and extracted with EtOH. The extracts were then chromatographed by silica gel flash chromatography (hexane, hexane/EtOAc (1:1), EtOAc, EtOAc (1:1), MeOH and MeOH/HOAc (98:2). The peptides were eluted with EtOAc/MeOH (1:1). Final purification was accomplished by repeated HPLC (RP C18) using MeCN/H$_2$O with 0.1% TFA (70–45% H$_2$O) (FIG. 1).

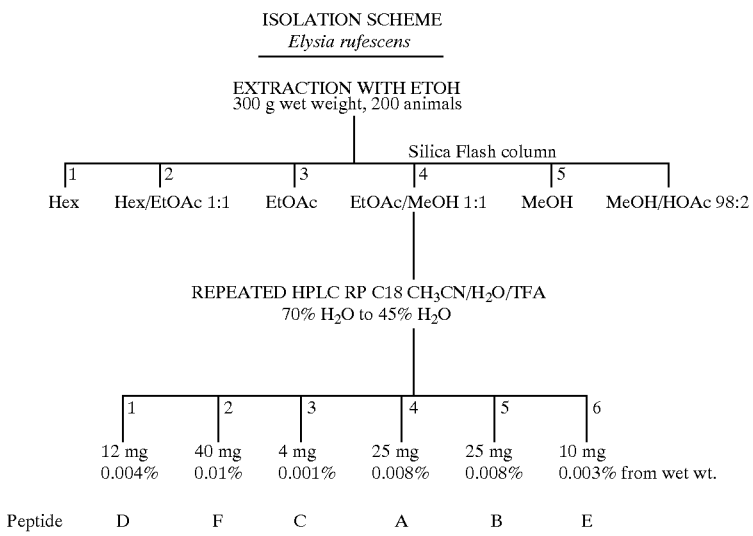

ISOLATION SCHEME
*Elysia rufescens*

The structures of the peptides were elucidated by 2NMR experiments (HMOC, HMBC, TOCSY, COSY and ROESY).

Kahalalide F was isolated as a white amorphous powder in 0.02% yield. A molecular formula of $C_{75}H_{1214}N_{14}O_{16}$ was deduced from detailed analyses of the $^{13}C$ and $^1H$ NMR spectra and the high resolution FAB mass spectrum. The 14 substructures in this compound arise from five valines, two isoleucines, two threonines, ornithine, dehydroaminobutyric acid, proline, phenilalanine and 5-methylhexanoic acid (5-MeHex). Kahalalide F is the largest peptide in this series of compounds.

EXPERIMENTAL

General Considerations

Optical rotations were measured on a Jasco DIP-370 digital polarimeter. Infrared spectra were recorded on a Nicolet MX-5 FTTR spectrometer. Gas chromatography was accomplsihed using a Hewlett-Packard Model 5890 instrument. Mass spectra were measured on a VG-70SE magnetic sector mass spectrometer. NMR spectra were measured on a General Electric QE-300 or a GN OMEGA 500 instrument. $^1H$ NMR chemical shifts are reported in ppm with the chemical shift of the residual protons of the solvent used as internal standards. $^{13}C$ NMR chemical shifts are reported in ppm by using the natural abundance $^{13}C$ of the solvent as an internal standard. Ultraviolet spectra were recorded on a Hewlett-Packard Model 8452A diode array spectrophotometer. All solvents were destilled from glass before use.

Two hundred sacoglossans (*Elysia rufescens*, FIG. 33) were collected at Black Point, O'ahu during April and May 1992, and extracted 3 times with EtOH. Spring appears to be the time of year *Elysia rufescens* is in greatest abundance at Black Point. The combined extracts were then chromatographed using silica gel flash chromatography (hexane, hexane/EtOAc (1:1). EtOAc, EtOAc/MeOH (1:1), MeOH, MeOH/HOAc (98:2). The depsipeptides were found in the EtOAc/MeOH (1:1) fraction. Repeated HPLC RP18 MeCN/ $H_2O$/TFA (55/45/1)—MeCN/$H_2O$/TFA ((30/70/1) yielded six new depsipeptides. For details see FIG. 1.

KAHALALIDE F

Final purification was accomplished by HPLC on RP18 MeCN/$H_2O$/TFA (55/45/1). Physical data: [α]D8°(c 4.32, MeOH); $^1H$ NMR (500 MHz, TFA/DMF); amino acid unit, δ (carbon position, mult, J): Val-1 4.16 (2, t, J=9.0 Hz), 7.11 (NH on 2, d, J=8.9 Hz), 1.77 (3, m), 0.95 (4, m), 0.95 (5, m); Dhb 9.20 (NH on 2, s), 6.48 (3, q, J=6.9 Hz), 1.43 (4, d, J=6.6 Hz); Phe 4.68 (2, q, J=6.6 Hz), 8.62 (NH on 2, d, J=6.6 Hz), 3.2 (3, dd, J=13.7, 7.2 Hz), 3.0 (3, dd, J=13.7, 9.0 Hz), 7.32 (5, d, J=7.2 Hz), 7.28 (6, t, J=7.5 Hz), 7.21 (7, t, J=7.2 Hz); Val-2 4.36 (2, m), 7.82 (NH on 2, d, J=6.6 Hz), 2.12 (3, m), 0.85 (4, m), 0.77 (5, d, J=6.6 Hz); Ileu-1 4.53 (2, m), 8.38 (NH on 2, d, J=9.6 Hz), 1.98 (3, m), 0.92 (4, d, J=6.6 Hz), 1.40 (5, m), 1.13 (5, m), 0.88 (6, t, J=7.2 Hz); Thr-1 4.63 (2, t, J=9.3 Hz), 8.12 (NH on 2, d, J=5.7), 5.07 (3, dq, 9.6, 6.0 Hz), 1.18 (4, d, J=6.3 Hz); Ileu-2 4.52 (2, m), 7.72 (NH on 2, d, J=8.4 Hz), 1.88 (3, m), 0.88 (4, d, J=6.3 Hz), 1.40 (5, m), 1.13 (5, m), 0.88 (6, d, J=7.2 Hz); Om 4.48 (2, m), 7.92 (NH on 2, d, J=7.8 Hz), 1.76 (3, m), 1.83 (4, m), 3.10 (5, p, J=5.1 Hz); Pro 4.42 (2, m), 2.12 (3, m), 1.97 (3, m), 2.02 (4, m), 1.88 (4, m), 3.75 (5, m), 3.68 (5, m); Val-3 4.41 (2, m), 7.90 (NH on 2, d, J=7.2 Hz), 2.12 (3, m), 0.95 (4, m), 0.85 (5, m); Val-4 4.34 (2, m), 7.68 (NH on 2, d, J=8.1 Hz), 2.17 (3, m), 0.95 (4, m), 0.90 (5, m); Thr-2 4.46 (2, m), 7.77 (NH on 2, d, J=8.1), 4.21 (3, dq, 6.3, 3.6 Hz), 1.12 (4, d, J=6.6); Val-5 4.32 (2, m), 7.85, (NH on 2, d, J=8.1 Hz), 7.82 (NH on (second conformation), d, J=8.1 Hz), 2.14 (3, m), 0.95 (4, m) 0.90 (5, m); 5-MeHex 2.26 (2, m), 1.60 (3, m), 1.20 (4, m), 1.55 (5, m), 0.87 (6, d, J=7.2 Hz), 0.87 (7, d, J=7.2 Hz); 5-MeHex 2.29 (2,m), 1.65 (3, m), 1.40 (3, m), 1.13 (4, m), 1.35 (5, m), 0.90 (6, m), 0.90 (7, m); $^{13}C$ NMR (125 MHz TFA/DMF): amino acid unit, δ (carbon position); Val-1 170.40 (1), 60.31 (2), 30.75 (3), 19.58 (4), 18.76 (5); Dhb 164.54 (1), 130.30 (2), 131.26 (3), 12.68 (4); Phe 171.31 (1), 56.27 (2), 36.79 (3), 138.23 (4), 129.86 (5), 128.77 (6), 126.98 (7); Val-2 172.94 (1), 58.57 (2), 32.38 (3), 18.92 (4), 17.60 (5); Ileu-1 171.87 (1), 57.48 (2), 38.78 (3), 14.56 (4), 26.78 (5), 11.67; Thr-1 169.68 (1), 57.37 (2), 71.05 (3), 17.34 (4); Ileu-2 171.92 (1), 57.29 (2), 38.01 (3), 14.78 (4), 26.55 (5), 11.63 (6); Om 172.01 (1), 52.87 (2), 29.63 (3), 24.39 (4), 40.05 (5); Pro 172.55 (1), 60.23 (2), 29.58 (3), 25.38 (4), 48.03 (5); Val-3 171.28 (1), 57.57 (2), 30.54 (3), 19.61 (4), 18.80 (5); Val-4 171.83 (1), 59.10 (2), 31.26 (3), 19.45 (4), 18.08 (5); Thr-2 170.97 (1), ,58.89 (2), 67.36 (3), 19.66 (4); Val-5 172.67 (1), 59.64 (2), 30.66 (3), 19.61 (4), 18.43 (5); 5-MeHex 173.83 (1), 36.28 (2), 23.99 (3), 38.96 (4), 28.10 (5), 22.54 (6), 22.50 (7); 5-MeHex (second conformation) 174.08 (1), 33.86 (2), 32.84 (3), 29.75 (4), 34.54 (5), 19.51 (6), 11.20 (7); IR neat (NaCl): 3287 (s, br), 2964 (s, br), 1646 (s), 1528 (s), 1465 (s), 1388 (m), 1228 (m), cm$^{-1}$; mass spectrum HRFAB m/z (fragment, %) 1477.9408 (M$^+$+1, 85) (calcd for C$_{75}$H$_{125}$N$_{14}$O$_{16}$:1477.9398); UV (MeOH): $\lambda_{max}$ 204 (89, 630)nm.

Amino acid analysis by GC-MS with a Chirasil-Val column indicates that Kahalalide F consists of D-Ileu, Om, L-Phe, D-Pro, L-Thr, D-Allo-Thr, 3 D-Val and 2-L-Val.

TABLE II $^1$H and $^{13}$C NMR Data for Kahalalide F (1) in DMF/TFA

| Amino Acid | Carbon | $^{13}$C, ppm$^a$ | Mult. | $^1$H, ppm$^b$ | Multiplicity |
|---|---|---|---|---|---|
| Valine-1 | 1 | 170.4 | s | (NH)7.11 | d, J=8.9 |
| | 2 | 60.3 | d | 4.16 | t, J=9.0 |
| | 3 | 30.8 | d | 1.77 | m |
| | 4 | 19.6 | q | 0.95 | m |
| | 5 | 18.8 | 1 | 0.95 | m |
| Dehydroamino- | 1 | 164.5 | s | (NH)9.20 | s |
| butyric acid | 2 | 130.3 | s | — | |
| | 3 | 131.3 | d | 6.48 | q, J=6.9 |
| | 4 | 12.7 | q | 1.43 | d, J=6.6 |
| Phenylalanine | 1 | 171.3 | s | (NH)8.62 | d, J=6.6 |
| | 2 | 56.3 | d | 4.68 | q, J=6.6 |
| | 3 | 36.8 | t | 3.23 | dd, J=13.7, 7.2 |
| | | | | 3.00 | dd, J=13.7, 9.0 |
| | 4 | 138.2 | s | | |
| | 5, 5' | 129.9 | d | 7.32 | d, J=7.2 |
| | 6, 6' | 128.8 | d | 7.28 | t, J=7.5 |
| | 7 | 127.0 | d | 7.21 | t, J=7.2 |
| Valine-2 | 1 | 172.9 | s | (NH)8.38 | d, J=6.6 |
| | 2 | 58.6 | d | 4.36 | m |
| | 3 | 32.4 | d | 2.12 | m |
| | 4 | 18.9 | q | 0.85 | m |
| | 5 | 17.6 | q | 0.77 | d, J=6.6 |
| Isoleucine-1 | 1 | 171.9 | s | (NH)8.38 | d, J=9.6 |
| | 2 | 57.5 | d | 4.53 | m |
| | 3 | 38.8 | d | 1.98 | m |
| | 4 | 14.6 | q | 0.92 | d, J=6.6 |
| | 5 | 26.8 | t | 1.40, 1.13 | m, m |
| | 6 | 11.7 | q | 0.88 | t, J=7.2 |
| Threonine-1 | 1 | 169.7 | s | (NH)7.72 | d, J=6.7 |
| | 2 | 57.4 | d | 4.63 | t, J=9.3 |
| | 3 | 71.1 | d | 5.07 | dq, J=9.6, 6.0 |
| | 4 | 17.3 | q | 1.18 | d, J=6.3 |
| Isoleucine-2 | 1 | 171.9 | s | (NH)7.72 | d, J=8.4 |
| | 2 | 57.3 | d | 4.52 | m |
| | 3 | 38.0 | d | 1.88 | m |
| | 4 | 14.8 | q | 0.88 | d, J=6.3 |
| | 5 | 26.6 | t | 1.40, 1.13 | m, m |
| | 6 | 11.6 | q | 0.88 | t, J=7.2 |
| Ornithine | 1 | 172.0 | s | (NH)7.92 | d, J=7.8 |
| | 2 | 52.9 | d | 4.48 | m |
| | 3 | 29.6 | t | 1.76 | m |
| | 4 | 24.4 | t | 1.83 | m |
| | 5 | 40.1 | t | 3.10 | p, 5.1 |
| Proline | 1 | 172.6 | s | | |
| | 2 | 60.2 | d | 4.42 | m |
| | 3 | 29.6 | t | 2.12, 1.97 | m, m |
| | 4 | 25.4 | t | 2.02, 1.88 | m, m |
| | 5 | 48.0 | t | 3.75, 3.68 | m, m |
| Valine-3 | 1 | 171.3 | s | (NH)7.90 | d, J=7.2 |
| | 2 | 57.6 | d | 4.41 | m |
| | 3 | 30.5 | d | 2.12 | m |
| | 4 | 19.6 | q | 0.95 | m |
| | 5 | 18.8 | q | 0.85 | m |
| Valine-4 | 1 | 171.8 | s | (NH)7.68 | d, J=8.1 |
| | 2 | 59.1 | d | 4.34 | m |
| | 3 | 31.3 | d | 2.17 | m |

TABLE II-continued $^1$H and $^{13}$C NMR Data for Kahalalide F (1) in DMF/TFA

| Amino Acid | Carbon | $^{13}$C, ppm$^a$ | Mult. | $^1$H, ppm$^b$ | Multiplicity |
|---|---|---|---|---|---|
| | 4 | 19.5 | q | 0.95 | m |
| Threonine-2 | 1 | 171.0 | s | (NH)7.77 | d, J=8.1 |
| | 2 | 58.9 | d | 4.46 | m |
| | 3 | 67.4 | d | 4.21 | dq, J=6.3, 3.6 |
| | 4 | 19.7 | q | 1.12 | d, J=6.6 |
| Valine-5 | 1 | 172.7 | s | (NH)7.85 | d, J=8.1 |
| | conf. #2 | | | (NH)7.82 | d, J=8.1 |
| | 2 | 59.6 | d | 4.32 | m |
| | 3 | 30.7 | d | 2.14 | m |
| | 4 | 19.6 | q | 0.95 | m |
| | 5 | 18.4 | q | 0.90 | m |
| 5-Methyl | 1 | 173.8 | s | | |
| Hexanoic acid | 2 | 36.3 | t | 2.26 | m |
| | 3 | 24.0 | t | 1.60 | m |
| | 4 | 39.0 | t | 1.20 | m |
| | 5 | 28.1 | d | 1.55 | m |
| | 6 | 22.5 | q | 0.87 | d, J=7.2 |
| | 7 | 22.5 | q | 0.87 | d, J=7.2 |
| 5-Methyl | 1 | 174.1 | s | | |
| Hexanoic acid | 2 | 33.9 | t | 2.29 | m |
| (second | 3 | 32.8 | 1 | 1.65, 1.40 | m |
| conformation) | 4 | 29.8 | t | 1.13 | m |
| | 5 | 34.5 | d | 1.35 | m |
| | 6 | 19.5 | q | 0.90 | m |
| | 7 | 11.2 | q | 0.90 | m |

$^a$at 125 MHz, DMF signal at 35.2 ppm;
$^b$at 500 MHz, DMF signal at 2.91 ppm.

TABLE I

In vitro Activity of Kahalalide F from *Elysia rufescens* Assay (M.I.C. μg/mL)

| Cytotoxicity μg/mL (IC$_{50}$) | |
|---|---|
| A-549 | 2.5 |
| HT-29 | 0.25–0.5 |
| Antiviral μg/mL (% reduction) | |
| Mv 1 Lu/HSV II | 0.5 (95%) |
| CV-1/HSV-1 | >8 |
| BHK/VSV | >8 |
| Antifungal 6 mm disk | 50 μg/disk |
| *Aspergillus oryzae* | 19 mm |
| *Penicillium notatum* | 26 mm |
| *Tricophyton mentagrophy* | 34 mm |
| *Saccharomyces cerevisiae* | neg |
| *Candida albicans* | 16 mm |

We claim:

1. A method of treating tumors in mammals comprising administering to a patient in need of such treatment, a therapeutic amount of the compound Kahalalide F, said compound having the following structure:

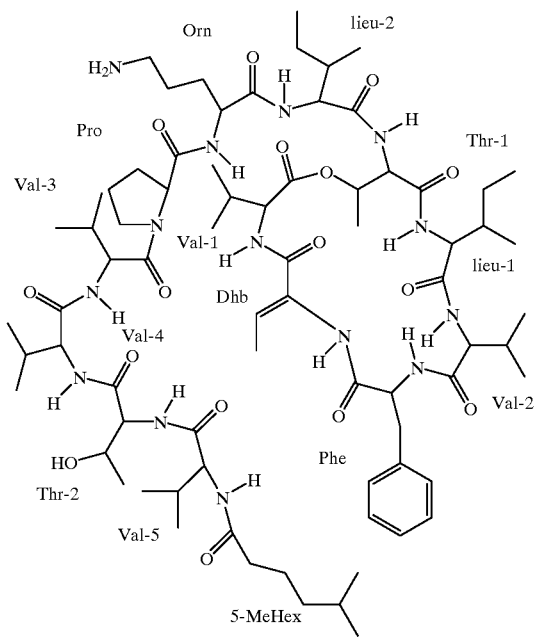

or a pharmaceutically acceptable salt thereof, wherein the tumor is human lung carcinoma.

2. A method of treating tumors in mammals comprising administering to a patient in need of such treatment, a therapeutic amount of the compound Kahalalide F, said compound having the following structure:

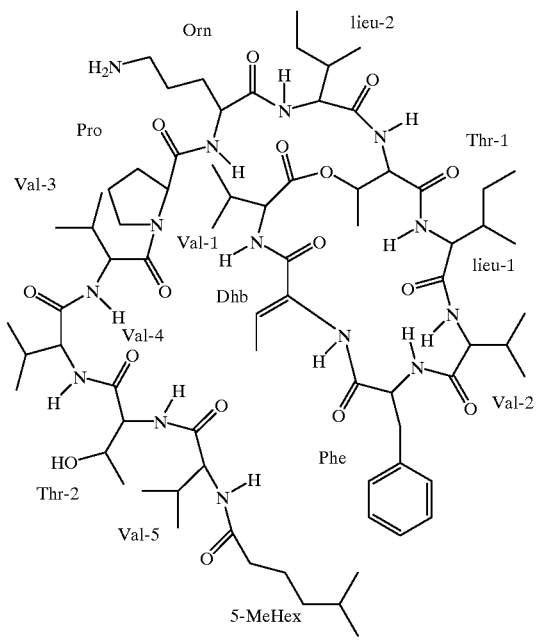

or a pharmaceutically acceptable salt thereof, wherein the tumor is human colon carcinoma.

3. A method of treating viral infections in mammals comprising administering to a patient in need of such treatment, a therapeutic amount of the compound Kahalalide F, said compound having the following structure:

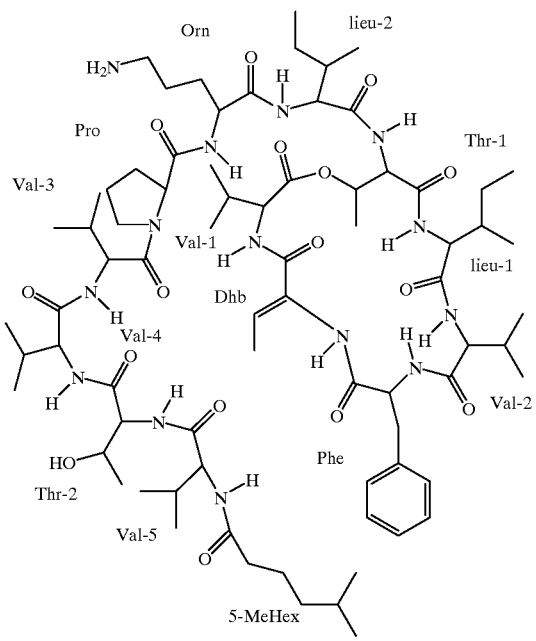

or a pharmaceutically acceptable salt thereof, wherein the virus is a Herpes simplex virus.

4. A method of treating viral infections in mammals comprising administering to a patient in need of such treatment a therapeutic amount of the compound Kahalalide F, said compound having the following structure:

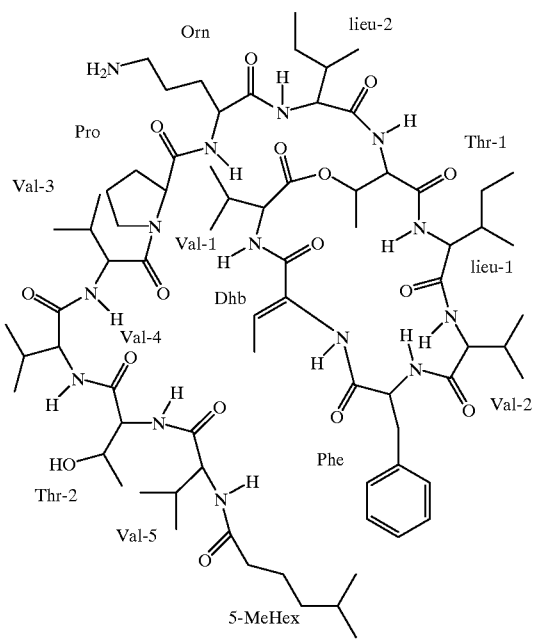

or a pharmaceutically acceptable salt thereof, wherein the virus is the Vesicular Stomatitis virus.

* * * * *